US008140365B2

(12) United States Patent
Springorum et al.

(10) Patent No.: US 8,140,365 B2
(45) Date of Patent: Mar. 20, 2012

(54) METHOD, SYSTEM, AND A COMPUTER READABLE MEDIUM FOR ADJUSTMENT OF ALTERABLE SEQUENCES WITHIN A DIAGNOSTIC WORKFLOW MANAGEMENT

(75) Inventors: Rudolf Theodoor Springorum, Eindhoven (NL); Frederik Visser, Eindhoven (NL); Jouke Smink, Eindhoven (NL); Leonardus Carolus Petrus Josephus Mollevanger, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 822 days.

(21) Appl. No.: 12/067,387

(22) PCT Filed: Sep. 21, 2006

(86) PCT No.: PCT/IB2006/053415
§ 371 (c)(1),
(2), (4) Date: Mar. 19, 2008

(87) PCT Pub. No.: WO2007/036854
PCT Pub. Date: Apr. 5, 2007

(65) Prior Publication Data
US 2010/0217617 A1  Aug. 26, 2010

(30) Foreign Application Priority Data
Sep. 29, 2005 (EP) .................................. 05109002

(51) Int. Cl.
*G06Q 2006/01* (2006.01)
(52) U.S. Cl. ..................... 705/7.11; 600/416; 600/921
(58) Field of Classification Search .................. 705/7, 8
See application file for complete search history.

(56) References Cited

U.S. PATENT DOCUMENTS

| 4,835,690 | A | * | 5/1989 | Gangarosa et al. | 600/410 |
|---|---|---|---|---|---|
| 5,341,318 | A | * | 8/1994 | Balkanski et al. | 708/402 |
| 5,406,476 | A | * | 4/1995 | Deziel et al. | 705/7.15 |
| 5,551,434 | A | * | 9/1996 | Iinuma | 600/455 |
| 5,786,816 | A | * | 7/1998 | Macrae et al. | 715/837 |
| 6,216,054 | B1 | * | 4/2001 | Jang et al. | 700/121 |
| 6,421,649 | B1 | * | 7/2002 | Rattner | 705/2 |
| 6,458,081 | B1 | * | 10/2002 | Matsui et al. | 600/437 |

(Continued)

FOREIGN PATENT DOCUMENTS

DE  101 14 017 A1  9/2001

(Continued)

OTHER PUBLICATIONS

Telescoping Series http://www.math.oregonstate.edu/home/programs/undergrad/CalculusQuestStudyGuides/SandS/SeriesTests/telescoping.html.*

(Continued)

*Primary Examiner* — Lynda Jasmin
*Assistant Examiner* — Octavian Rotaru

(57) ABSTRACT

In a workflow management method and apparatus, one or more computers are programmed to receive an original sequence, such as a scan sequence which controls a diagnostic scanner to perform an imaging procedure. An available time span within which to perform the original sequence is also received. The available time span is compared with a duration of the original scan sequence. If the original scan sequence duration is longer than the available time span, one or more alterable subsequences of the original sequence are shortened to create an adjusted scan sequence that fits into the available time span.

14 Claims, 5 Drawing Sheets

U.S. PATENT DOCUMENTS

Figure 1:
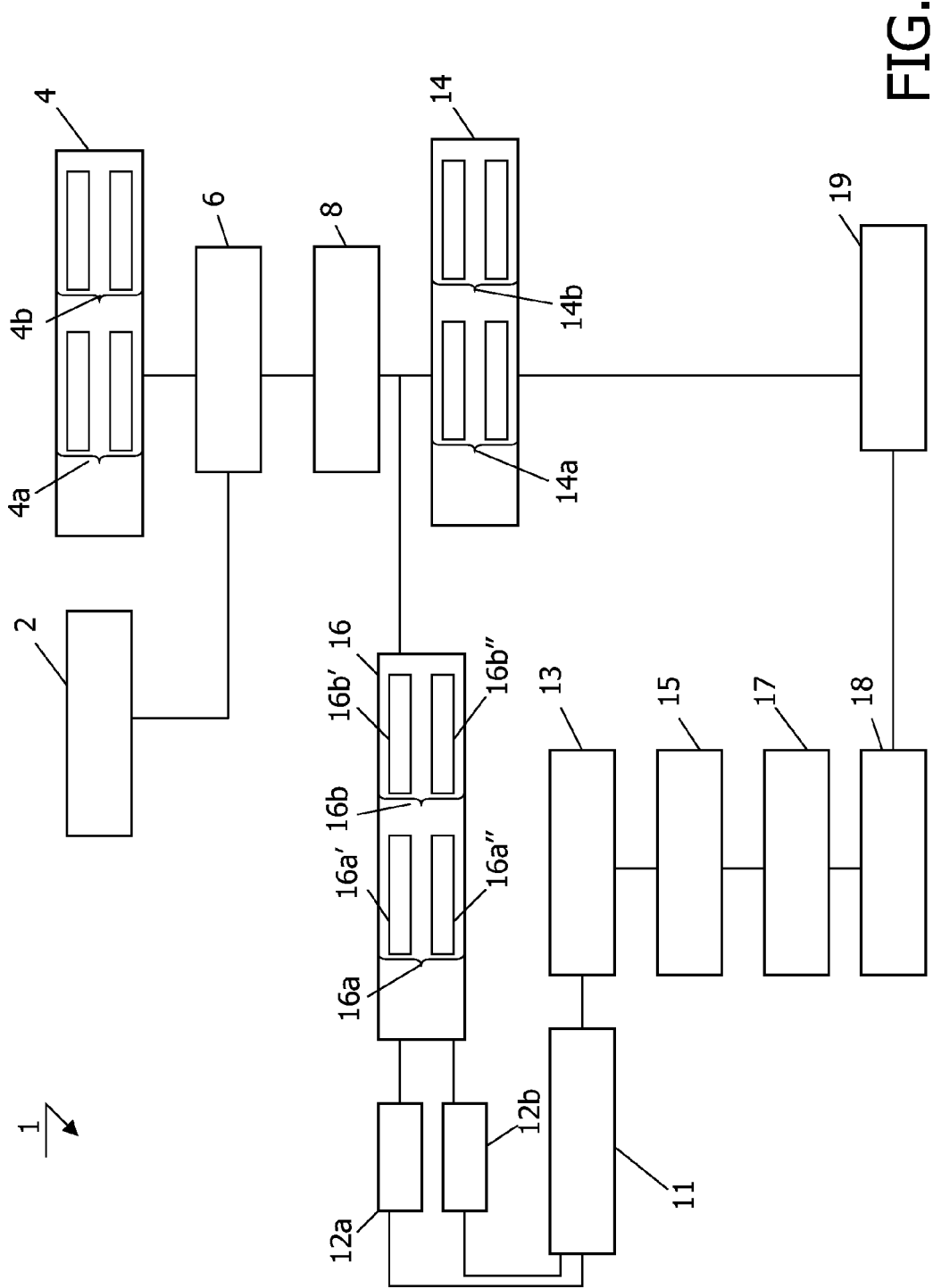

| | | | |
|---|---|---|---|
| 6,574,629 B1* | 6/2003 | Cooke, Jr. et al. | 1/1 |
| 6,603,494 B1* | 8/2003 | Banks et al. | 715/807 |
| 6,904,161 B1* | 6/2005 | Becker et al. | 382/128 |
| 7,020,844 B2* | 3/2006 | Trevino et al. | 715/772 |
| 7,260,547 B2* | 8/2007 | Kameda | 705/3 |
| 7,460,984 B1* | 12/2008 | Clark et al. | 703/2 |
| 7,464,373 B1* | 12/2008 | Yunt et al. | 717/125 |
| 7,522,744 B2* | 4/2009 | Bai et al. | 382/100 |
| 7,835,895 B1* | 11/2010 | Orofino et al. | 703/13 |
| 2002/0046062 A1 | 4/2002 | Kameda | |
| 2002/0099571 A1* | 7/2002 | Waku et al. | 705/2 |
| 2002/0198454 A1* | 12/2002 | Seward et al. | 600/437 |
| 2003/0050801 A1* | 3/2003 | Ries et al. | 705/2 |
| 2003/0095150 A1 | 5/2003 | Trevino et al. | |
| 2003/0195774 A1 | 10/2003 | Abbo | |
| 2004/0024303 A1* | 2/2004 | Banks et al. | 600/407 |
| 2004/0267575 A1* | 12/2004 | Boing | 705/3 |
| 2005/0107998 A1* | 5/2005 | McLernon et al. | 703/22 |
| 2005/0114178 A1* | 5/2005 | Krishnamurthy et al. | 705/2 |
| 2006/0031095 A1* | 2/2006 | Barth et al. | 705/2 |
| 2008/0108895 A1* | 5/2008 | Sabol et al. | 600/425 |
| 2009/0150184 A1* | 6/2009 | Spahn | 705/3 |

FOREIGN PATENT DOCUMENTS

| | | |
|---|---|---|
| DE | 101 25 504 A1 | 12/2002 |
| EP | 1 443 444 A2 | 8/2004 |
| WO | WO 97/15022 A1 | 4/1997 |
| WO | WO 02/39899 A2 | 5/2002 |
| WO | WO 02/095653 A2 | 11/2002 |

OTHER PUBLICATIONS

Workflow analysis and modeling in medical IT projects, Medicamundi 46-2, Aug. 2002 http://www.healthcare.philips.com/phpwc/main/about/assets/docs/medicamundi/mm_vol46_no2/ouvry.pdf.*

Workflow management, integration technology for efficient radiology, Medicamundi 45-4, Nov. 2001 http://www.healthcare.philips.com/phpwc/main/about/assets/docs/medicamundi/mm_vol45_no4/mm_45-4_workflow.pdf.*

Anzbock et al, Modeling and Implementing Medical e-services, Technical University of Vienna, TUV-1841-2004-14, Aug. 2004 http://www.infosys.tuwien.ac.at/Staff/sd/papers/TUV-1841-2004-14.pdf.*

Greiner et al, Adaptive Guideline-based Treatment Workflows with AdaptFlow, proceedings of symposium on computerized guidelines and protocols, p. 113-117, CGP 2004 http://dbs.uni-leipzig.de/file/cgp04-12.1.pdf.*

Muller et al, AgentWork—A workflow system supporting rule-based workflow adaptation, Data and Knowledge Engineering, 2004.*

Bertermann et al, The Implementation of syngo to Improve the Workflow in the MRI Department of a Large General Radiology Practice, electromedica 71, No. 1, 2003 http://www.medical.siemens.com/siemens/en_US/rg_marcom_FBAs/files/Press_Releases/Whitepapers/4.electromedica.pdf.*

SOMATOM Sensation 64 Application Guide Protocols Principles Helpful Hints Software Version syngo CT 2005A printed in Germany Sep. 2004.*

Bertermann et al., Added Value Through Process Optimization: The Implementation of syngo to Improve the Workflow in the MRI Department of a Large General Radiology Practice Electromedica No. 71, 2003, No. 1.*

Maynart Operations Sequence Technique book by Kjell B. Zandin MOST work measurement systems ISBN 0-8247-0953-5.*

Feedback Mechanism and Algebraic Loops http://www.20sim.com/webhelp/editor/compiling/algebraicloops.htm.*

* cited by examiner

METHOD, SYSTEM, AND A COMPUTER READABLE MEDIUM FOR ADJUSTMENT OF ALTERABLE SEQUENCES WITHIN A DIAGNOSTIC WORKFLOW MANAGEMENT

The invention relates to method for diagnostic workflow management, said method comprising the step of accessing a template comprising a sequence of handlings with their corresponding durations.

The invention further relates to system for diagnostic workflow management, said system comprising an input for accessing a template comprising sequence of handlings with their corresponding durations and for accessing available time span for executing said sequence.

The invention still further relates to a medical diagnostic apparatus arranged to carry out a sequence of handlings.

The invention still further relates to a computer program for enabling a diagnostic workflow management, said method comprising instructions for causing a processor to carry out the steps of accessing a template comprising a sequence of handlings with their corresponding durations.

The invention still further relates to graphic user interface for enabling a diagnostic workflow management, said workflow comprising a sequence of handlings.

An embodiment of the method as is set forth in the opening paragraph is known from US2004/0267575. The known method is arranged to monitor a sequence of diagnostic handlings, whereby time data for the sequence is established, comprising starting point of the sequence, duration of a planned work process, estimated remaining time for the work process, end time of the work process. In particular, a personal time lapse plan assigned to a patient in question is determined based on available time data and can be projected using a suitable graphic user interface. Thus, the known method is arranged to monitor a workflow and to provide an update on the progress within selected working process. The known method operates with estimates of the time necessary for each handling within the sequence. With this respect the known method uses a learning system which estimates an average time spent by a patient on a modality, like CT or MRI, based on a plurality of similar studies, presenting a most statistically probable value.

It is a disadvantage of the known method that it is not suitable for coping with a sudden variation of the time span available for implementing pre-planned sequences. For example, in a typical hospital environment patients are scheduled for the day. Circumstances can lead to changes in the schedule and delays in examinations. The patient may arrive late or the previous examination needs to be extended for a few more scans due to pathology findings. The operators are then forced to manipulate scan parameters in order to cut down the duration of each individual scan to catch up the patient schedule. It is, however, acknowledged that the image quality of a scan is proportional to the scan time. Therefore, the operator tries to balance between available time on one hand and the image quality on the other hand. Manipulating scan parameters can be tedious and not obvious to do as it influences a plurality of scan characteristics. The spatial or temporal resolution might change as well as image contrast, signal to noise ratio or artifact sensitivity. This dependence of the image quality characteristics on acquisition time is particularly important for magnetic resonance imaging.

It is an object of the invention to provide a method for diagnostic workflow management, whereby a user is enabled to change duration of a handling in the sequence in an easy and reliable way, not causing substantial deterioration of the image quality.

The method according to the invention comprises the further steps of
  accessing available time span for executing said sequence;
  calculating a difference between said available time span and a sum of said corresponding durations;
  assigning an allowable duration for said sequence based on said difference;
  adjusting the sequence yielding adjusted sequence temporally fitting into the allowable duration.

Preferably, the available time span for executing of the exam is loaded electronically, for example, from Radiological Information System (RIS), or, alternatively it may be accessed from any suitable user interface arranged to support data input. It is a usual practice to prepare a template of sequence handlings, like a sequence of data acquisition scan for MR, X-ray or CT acquisitions. Likewise, the sequence handling may be accessed from another source, like a nuclear medicine investigation plan, or an ultra-sound study log. The method according to the invention will be further discussed with reference to a MR scanner, without limiting the scope of possible applications. MRI scanners are used to perform a medical examination of the human body. Such a patient examination consists of several acquisition steps also known as scans. Each of these scans exists of a set of examination parameters. Scan parameter values are stored in a database such that the user can easily select the desired preset procedures to perform the examination. The precise scans used for a clinical examination depend on the clinical application.

By using the template for sequence of handlings the user is allowed to store all preset procedures that belong to a clinical examination in a database. This allows the user to quickly select the entire examination at once directly from a database. Such templates comprise additional information than just the set of preset procedures such as the order with which the scans need to be carried out. Scans that should be performed using the same geometrical planning are identified as such and prevent the user from unnecessary geometrical planning steps.

A typical parameter of a scan is it's duration. The duration of these preset procedures differ from a few seconds up to several minutes or more. A typical generic examination consists of a quick survey scan that takes a few seconds only, followed by three or more high detailed scans that last for three, four or five minutes each. The total examination duration can be calculated by adding all the individual scan durations together. With the implementation of automated planning the duration of automated planning steps can be calculated in real time or beforehand.

Only a small fraction of the total examination time remains uncertain such as iterative processes during preparation phases or patient dependencies such as recovery times in between successive breath-holds or contrast arrival times for perfusion and angiography scans. Not every part of an examination may have a fixed duration. Some procedures such as preparation phases use iterative processes for their optimizations. In those cases the duration of a preparation phase can be estimated beforehand based upon previous preparation experiences. The corresponding data is stored in the template for handling and is used as such. For some preparative handlings time-out parameters are specified which could be used to estimate the maximum duration of an optimization step for a certain handling. For breath-hold scans the duration in between successive breath-hold scans is estimated based on assumptions for breath-hold recovery times. When automated breath-hold commands are given also these times in between scans are known on beforehand. For other patient dependent timings, such as contrast arrival times, the duration is estimated based upon previous experiences in similar templates or based on assumptions.

A suitable user interface can be provided to specify the available time span to carry out the envisaged handling. This feature can be implemented using one of the following options: a) the remaining time available is specified directly; b) total examination duration is specified after which the elapsed time is subtracted resulting in the remaining examination time available c) new end-time for an examination is specified directly, whereby available remaining examination duration is calculated by subtracting the current time from the end-time d) user specifies the amount of scan time reduction as a fraction or percentage.

When both time span and total duration of envisaged handlings are known, a difference between them is calculated. It is noted that although the preferred embodiment of the invention considers a shortage of time available for execution of the handlings, it is also possible that a surplus of time is available. In the former case the allowable duration will be shorter than afore planned and in the latter case the allowable duration will be longer than afore planned. At the final step of the method according to the invention, the sequence is adjusted to fit into a tighter schedule or to expand handlings to use the available time most optimally. Preferably, the step of adjusting the sequence is performed using a suitable optimization routine which optimizes a parameter "scan time" while keeping other parameters, like spatial or temporal resolution, expected image contrast, signal to noise ratio or artifact sensitivity within predetermined acceptable level. Preferably, for sequence shortening procedure, such acceptable level is kept between 85-100% of the expected value for not adjusted sequence.

In an embodiment of the method according to the invention, the step of adjusting the sequence comprises the steps of
  identifying unalterable sub-sequence within said sequence;
  subtracting duration of the unalterable sub-sequence from the allowable duration yielding further allowable duration;
  adjusting remaining sub-sequence within said sequence yielding adjusted sub-sequence temporally fitting into said further allowable duration;
  combining unalterable sub-sequence with adjusted sub-sequence yielding adjusted sequence.

This technical measure is based on the following insight. For some scans the duration cannot be changed. Therefore, such scans must be recognized automatically. These scans serve a specific feature whereby the reproducibility of these scans is essential for the image quality. Such scans include: SENSE reference scans that are used for coil sensitivity calibration; scout scans to be used for automated planning, elapsed scans, critical contrast enhanced angiography scans or other scans for which changing parameters is prohibited for the user.

According to the present embodiment of the method according to the invention new scan durations are calculated for the remaining scans based upon the remaining examination time available. Unchangeable scans are recognized as such and remain unchanged. Preparation phases, reconstruction durations (when applicable) breath-hold recovery times in between successive breath-hold scans and other overhead times are preferably included in the calculations and remain unchanged.

In a further embodiment of the method according to the invention the step of identifying unalterable sub-sequence within said sequence is carried out automatically.

For this purpose the method according to the invention may use a suitable computer program arranged to detect a certain inhibitor tag in the handling protocol. This feature can be easily implemented using DICOM protocol, which provides information not only on scan data, like orientation, geometry, duration, but also on a status of the scan (done or in preparation) and the type of the scan (angiography, preparation phase, reconstruction and so on). The computer program identifies the parts of the handling sequence for which the duration can be changed. This feature improves reliability of the adjusting step as it ensures that the user does not overlook important information.

In a still further embodiment of the method according to the invention the method comprises the step of prompting the user for acceptance of the adjusted sequence.

It is particularly advantageous to build a control loop, whereby the user is enabled to accept the proposed adjustment of the sequence of handlings and to alter the scans which adjustment was inhibited or to mark new scans which should also be protected from alteration. Preferably, this feature is implemented as a checkbox-option in a suitable graphic user interface.

In a still further embodiment of the method according to the invention, the method comprises the step of executing the adjusted sequence within the allowable duration. As has been noticed earlier, a variety of suitable sequences of handlings is envisaged, including data acquisition using MR, X-ray or CT apparatus. Likewise, the sequence handling may be implemented on a nuclear medicine investigation unit, or an ultrasound diagnostic apparatus. Likewise, this procedure may be extended and can be applied across multiple examinations.

A system for diagnostic workflow management according to the invention comprises:
  computing means for calculating a difference between said available time span and a sum of corresponding durations;
  processing means for assigning an allowable duration for said sequence based on said difference;
  optimization means for adjusting the sequence to temporally fit into the allowable duration.

Preferably, the system according to the invention is implemented as a control unit with is arranged in electronic communication with a suitable data acquisition unit. The computing means of the system according to the invention is preferably implemented as an electronic calculator for computing a difference between the available time span and a sum of corresponding durations of individual handlings within the selected sequence. Processing means of the system according to the invention is arranged to assign the allowable duration for the sequence based on said difference. The allowable duration may be shorter than initially envisaged due to a lack of time, or, alternatively, it may be longer than the initially envisaged duration due to surplus of available time. Preferably, the system according to the invention further comprises a tagging means arranged to inhibit a sub-sequence from being altered. The tagging means may be implemented as a computer code for searching handling's entries for pre-determined flags, like type of handling, its planned time, its status or the like. Preferably, the handling entries are stored in DICOM format.

The invention still further relates to a medical diagnostic apparatus comprising the system for diagnostic workflow management as is discussed with reference to the foregoing.

A computer program for enabling a diagnostic workflow management according to the invention comprises instructions for causing a processor to carry out the following steps:

accessing a template comprising a sequence of handlings with their corresponding durations;
accessing available time span for executing said sequence;
calculating a difference between said available time span and a sum of corresponding durations;
assigning an allowable duration for said sequence based on said difference;
adjusting the sequence yielding adjusted sequence temporally fitting into the allowable duration.

The computer program according to the invention provides automatic means for adjustment of the sequence of handlings, being advantageously sophisticate tool to cope with mismatch between available and planned times for executing said sequence.

Preferably, the computer program according to the invention comprises further instructions of
identifying unalterable sub-sequence within said sequence;
subtracting duration of the unalterable sub-sequence from the allowable duration yielding further allowable duration;
adjusting remaining sub-sequence within said sequence to temporally fit into said further allowable duration;
combining unaltered sub-sequence with adjusted sub-sequence yielding adjusted sequence.

Present embodiment of the computer program according to the invention is particularly advantageous for situations where the sequence comprises temporally critical handlings, or handlings which are already executed. Still preferably, for the step of identifying unalterable sub-sequence within said acquisition steps a graphic user interface is used.

The graphic user interface according to the invention comprises:
a plurality of editable fields arranged to feed back to the user a sequence of handlings together with their respective durations;
data input means arranged to enable an input of allowable time span for carrying out said sequence;
first feedback means arranged to display a difference between the time span and the sum of said durations;
second feedback means arranged to prompt the user for accepting the sequence.

The graphic user interface (GUI) according to the invention provides user means for accurately adjust the sequence of handlings when there is a mismatch between available time span for executing a sequence of handlings and a sum of respective durations of individual handlings. A user interface is preferably provided such that the user can specify the desired total or remaining examination duration or the desired end-time of the examination. This is preferably implemented using a graphical representation of scans on a timeline. When the GUI is connected to a RIS additional information such as time schedules can be retrieved automatically. In this case the end-time is already known and the user doesn't need to specify the desired end-time anymore. The desired end-time is preferably taken over from the RIS by default, still allowing the user to make changes in end-time or remaining examination duration.

In an embodiment of the graphic user interface the second feedback means is further arranged to communicate with a sequence adjustment module and to prompt the user for accepting the adjusted sequence.

For some handlings comprising scans the user may not want a workflow management system to manage it's duration automatically. A user interface is provided such that the user can protect those scans from shortening strategies. This feature is preferably implemented as a checkbox-option. Optionally, the user interface may be arranged such that the user can make a sub selection of scans for which time shortening will be applied.

These and other features of the invention will be discussed with reference to figures.

FIG. 1 presents in a schematic way an embodiment of a flow-chart exemplifying the method according to the invention.

Figure 2:
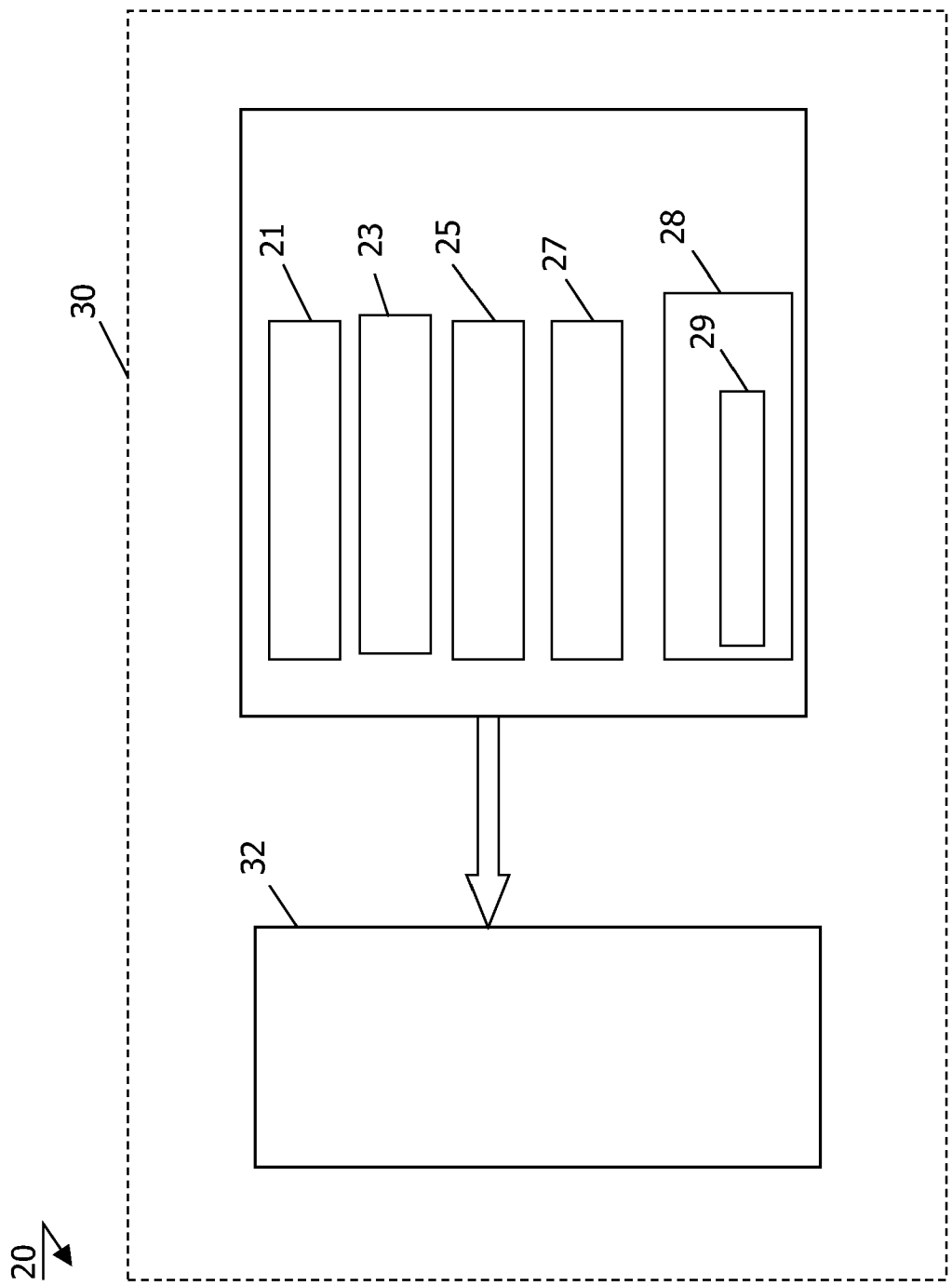

FIG. 2 presents in a schematic way an embodiment of a system according to the invention.

Figure 3:
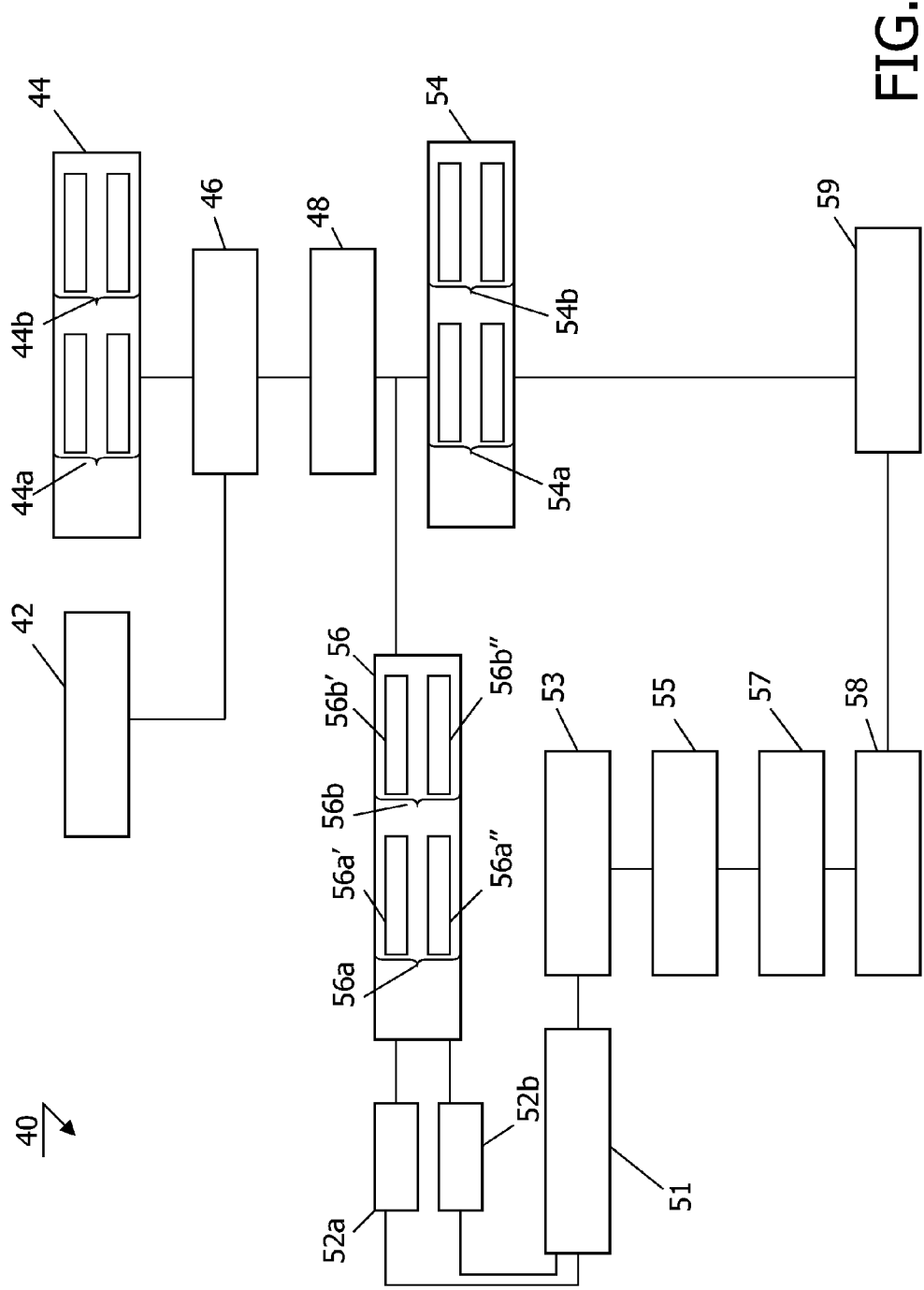

FIG. 3 presents in a schematic way an embodiment of a flow-chart exemplifying the computer program according to the invention.

Figure 4:
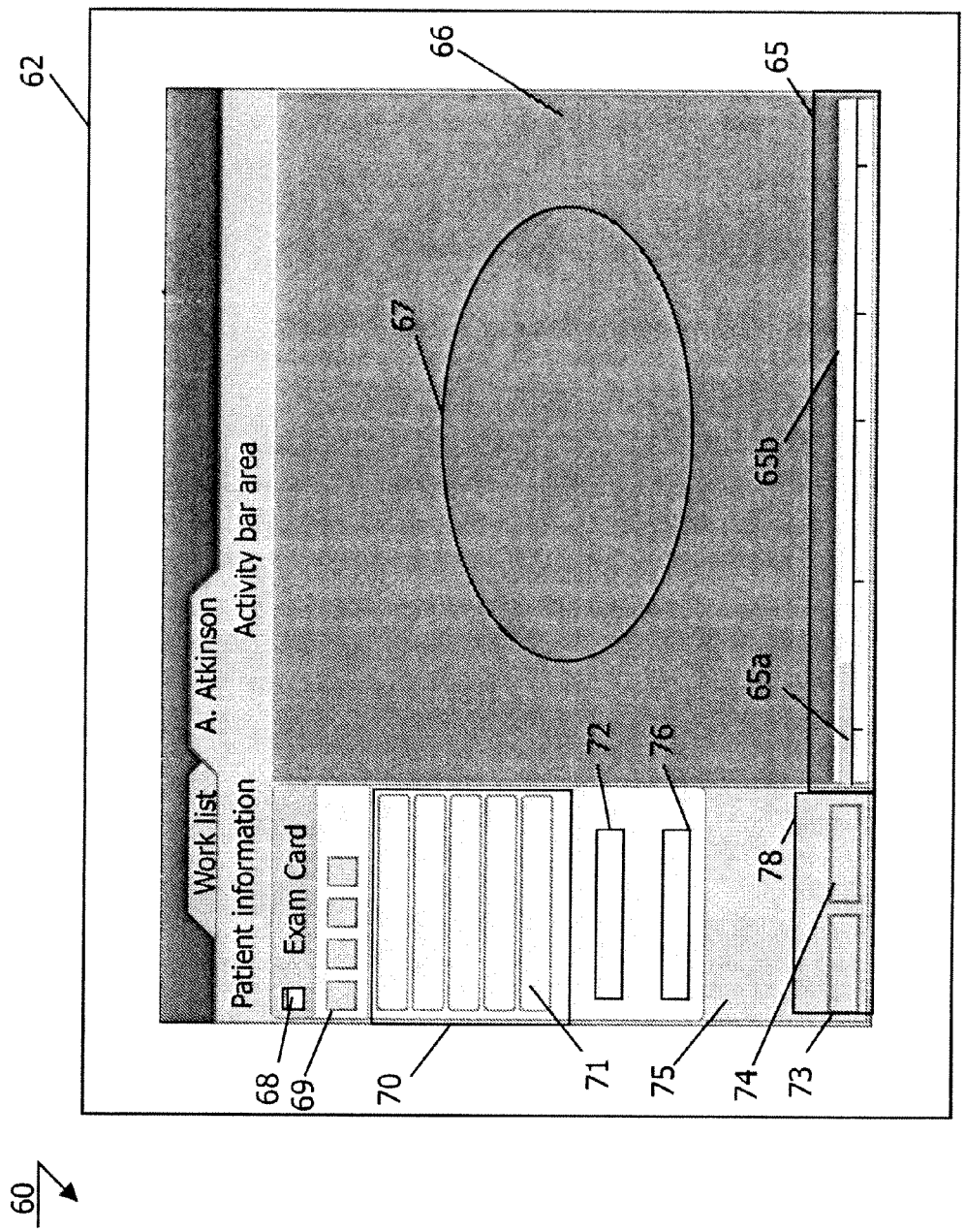

FIG. 4 presents in a schematic way an embodiment of a graphic user interface according to the invention.

Figure 5:
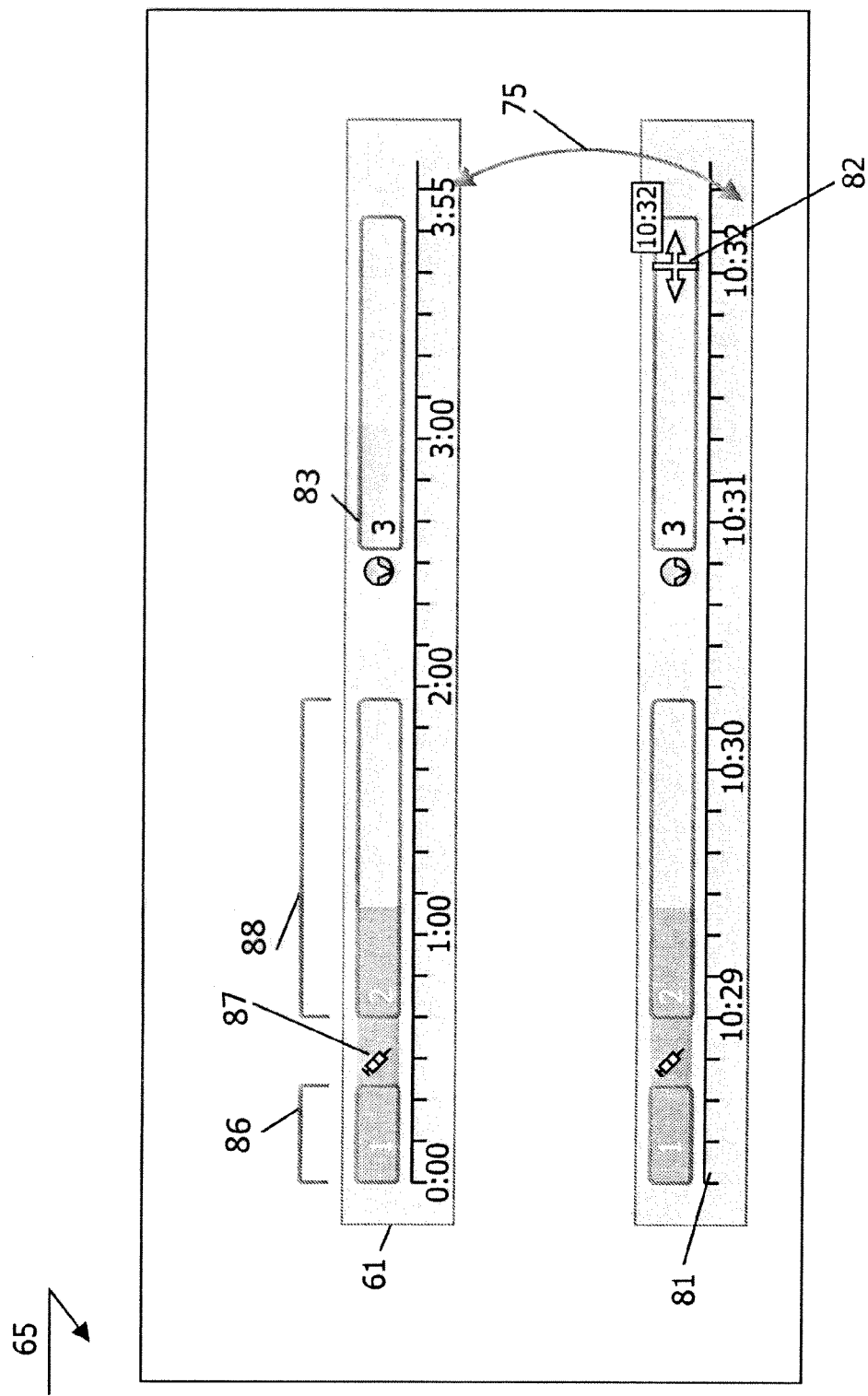

FIG. 5 presents in a schematic way an embodiment of a time diagram representing the sequence.

FIG. 1 presents in a schematic way an embodiment of a flow-chart exemplifying the method according to the invention. According to the method 1 of the invention, at step 2 an available time for executing a sequence of handlings is accessed. Preferably, the available time span is accessed automatically by electronic means. Alternatively, it may be accessed from an interactive input-output device, like a keyboard. At step 4 the template comprising the sequence of handlings 4a is accessed, whereby each handling is assigned its corresponding duration 4b. At step 6 a difference between the available time span and a sum of said corresponding durations is calculated, whereas at step 8 an allowable duration for executing the sequence is assigned based on said difference. The method according to the invention is suitable for coping with the situation when the available time is smaller than the sum of corresponding durations, or when the available time span is greater than the sum of corresponding durations, both cases being contemplated. At step 14 of the method according to the invention, the sequence 4a is adjusted yielding the adjusted sequence 14a, which integral duration 14b fits into the available time span, as given at step 2. Preferably, the step of adjusting the sequence 14 is performed using a suitable optimization routine (not shown) which is arranged to optimize a parameter "scan time" while keeping other parameters within acceptable level. Examples of such parameters are spatial or temporal resolution, expected image contrast, signal to noise ratio, artifact sensitivity, etc.

It is possible that in some circumstances that it is not desirable to adjust every handling within the selected sequence. In this case, the method according to the invention after step 8 proceeds to step 16, whereat unalterable sub-sequence 16a' within said sequence 16a is detected. The respective duration 16b' of the unalterable handling 16a' is detected as well. Furtheron at step 13, the duration 16b' is subtracted from the allowable duration yielding further allowable duration and the remaining sub-sequence 16a" is adjusted at step 15 so that it's cumulative duration 16b" fits into the further allowable duration. As a result, the corresponding sub-sequences 16a' and 16a" are combined at step 17 yielding thus adjusted sequence 16a at step 18 fitting into the allowable duration as determined at step 8. Preferably, the unalterable handling is identified at step 12a by automatic means. Alternatively, it can be assigned as such by the user interactively at step 12b. Still preferably, at step 11 the user is prompted on the assignment of the unalterable handling for quality control purposes. Still preferably the adjusted sequence is executed at step 19.

FIG. 2 presents in a schematic way an embodiment of a system 20 according to the invention. The system for diagnostic workflow management according to the invention comprises an input 21 for accessing a template (not shown) comprising a sequence of handlings with their corresponding durations and for accessing available time span (not shown) for executing said sequence. The system 20 further comprises computing means 23 for calculating a difference between said available time span and a sum of corresponding durations, processing means 25 for assigning an allowable duration for said sequence based on said difference, optimization means 27 for adjusting the sequence to temporally fit into the allowable duration.

Preferably, the system according to the invention is implemented as a control unit with is arranged in electronic communication with a suitable data acquisition unit 32 of a medical apparatus 30. The computing means 23 of the system according to the invention is preferably implemented as an electronic calculator for computing a difference between the available time span and a sum of corresponding durations of individual handlings within the selected sequence. Processing means 25 of the system according to the invention is arranged to assign the allowable duration for the sequence based on said difference. The allowable duration may be shorter than initially envisaged due to a lack of time, or, alternatively, it may be longer than the initially envisaged duration due to surplus of available time. Preferably, the system 20 according to the invention further comprises a tagging means 28 arranged to inhibit a sub-sequence (not shown) from being altered. The tagging means may be implemented as a computer code 29 for searching handling's entries for pre-determined flags, like type of handling, its planned time, its status or the like. Preferably, the handling entries are stored in DICOM format.

FIG. 3 presents in a schematic way an embodiment of a flow-chart exemplifying the computer program according to the invention. The computer program 40 for enabling a diagnostic workflow management according to the invention comprises instructions for causing a processor (not shown) to carry out the following steps: at step 44 a template comprising a sequence of handlings 44a with their respective durations 44b is accessed; at step 42 an available time span for executing said sequence is accessed. At step 46 a difference between said available time span and a sum of corresponding duration is calculated, whereby at step 48 an allowable duration for executing said sequence is assigned based on said difference. At step 54 the sequence is adjusted yielding adjusted sequence 54a with adjusted respective durations 54b by temporally fitting respective handlings thus fitting into said allowable duration. Preferably, the step of adjusting the sequence at step 54 is performed using a suitable optimization routine (not shown) which is arranged to optimize a parameter "scan time" while keeping other parameters within acceptable level. Examples of such parameters are spatial or temporal resolution, expected image contrast, signal to noise ratio, artifact sensitivity, etc.

Preferably, for circumstances when it is not desirable to adjust every handling within the selected sequence, the computer program 40 according to the invention after step 48 proceeds to step 56, whereat unalterable sub-sequence 56a' within said sequence 56a is detected. The respective duration 56b' of the unalterable handling 56a' is detected as well. Furtheron at step 53, the duration 56b' is subtracted from the allowable duration yielding further allowable duration and the remaining sub-sequence 56a" is adjusted at step 55 so that it's cumulative duration 56b" fits into the further allowable duration. As a result, the corresponding sub-sequences 56a' and 56a" are combined at step 57 yielding thus adjusted sequence at step 58 fitting into the allowable duration as determined at step 48. Preferably, the unalterable handling is identified at step 52a by automatic means using suitable subroutines. A suitable example of such subroutine is a tag detector implemented, for example, as a DICOM reader. Alternatively, it can be assigned as such by the user interactively at step 52b. Still preferably, at step 51 the user is prompted using suitable user interface means (not shown) on the assignment of the unalterable handling for quality control purposes. Still preferably the computer program 40 according to the invention further comprises an instruction for a suitable data acquisition system to execute the adjusted sequence at step 59.

FIG. 4 presents in a schematic way an embodiment of a graphic user interlace according to the invention. The graphic user interface 60 is arranged for enabling a diagnostic workflow management comprising of a sequence of handlings. For this purpose the graphic user interface 60 is being projected on a suitable display 62. The graphic user interlace 60 comprises a plurality of editable fields 70 arranged to feed back to the user a sequence of handlings together with their respective durations 71. Preferably, such sequence is stored in a suitable database 68 and can be loaded using a suitable data input means 69, preferably arranged by a patient name. In addition, the graphic user interface 60 comprises a first feed back means 72 arranged to display a difference between the time span and the sum of said durations. Further, the graphic user interface 60 comprises a second feedback means 76 arranged to prompt the user for accepting the adjusted sequence. The second feedback means 76 is preferably arranged to communicate with a sequence adjustment module 78 and to prompt the user for accepting the adjusted sequence. An example of a suitable sequence adjustment module is a computer code arranged to implement an optimization algorithm for adjusting respective durations of handlings constituting the sequence.

The graphic user interface 60 preferably still further comprises a graphics window 66 whereto next to an image area 67 information on a sequence implementation scheme 65 is given, whereby a diagram of the entire sequence is given, including current progress information 65a, 65b. Details of the sequence diagram are discussed with reference to FIG. 5.

Preferably, the graphic user interface according to the invention further comprises tagging means 73, 74 arranged to select a sub-sequence within current sequence which may not be adjusted. The tagging means 73 may be implemented as a computer program arranged to automatically select the non-adjustable handlings, whereas the tagging means 74 may be arranged to enable a manual selection or de-selection of the handlings. When the handlings which may not me adjusted are selected, the graphic user interface according to the invention preferably prompts the user on confirmation of the selection using second feedback means 76.

FIG. 5 presents in a schematic way an embodiment of a time diagram 65 representing the sequence. Preferably, it is possible to switch between the scan time 61 and the real time 81. the switching operation 75 can be enabled by an actuatable button (not shown) in the graphic user interface 60 of FIG. 4. Alternatively, both scan time diagram 61 and real time diagram 81 can be shown. The scan time diagram 61 is preferably arranged to feed back the information on the respective handlings 86, 88, 83 and time between data acquisitions 87. Preferably, in case when an additional patient manipulation is taking place, like contrast delivery, the corresponding time instant is also presented by means of a suitable indicator, like an icon. Preferably, the real time diagram 81 further comprises a suitable indicator of current time 82 for user's convenience.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of medical diagnostic imaging workflow management for controlling a medical diagnostic imaging scanner, said method comprising the steps of:
accessing a template including a medical diagnostic imaging scan sequence which controls a medical diagnostic imaging scanner to perform a medical diagnostic imaging scan on a patient. the templated scan sequence including alterable and unalterable subsequences with their corresponding durations;
accessing an available time span for executing said medical diagnostic imaging scan sequence template;
calculating a difference between said available time span and a sum of the scan subsequence durations in said medical imaging scan template;
determining an allowable duration for said medical diagnostic imaging scan sequence based on said difference;
optimizing by one or more computers the medical diagnostic imaging scan sequence of said template to fit into the allowable duration by:
identifying the unalterable sub-sequences within said medical diagnostic imaging scan sequence;
subtracting the unalterable sub-sequence durations from the allowable duration yielding a remaining duration;
automatically adjusting the duration of at least one of the alterable sub-sequence within said medical diagnostic imaging scan sequence template yielding one or more adjusted alterable sub-sequences which temporally fits into said remaining duration;
combining unalterable sub-sequences with the adjusted alterable sub-sequences yielding an adjusted medical diagnostic imaging scan sequence;
controlling a medical diagnostic imaging scanner with the adjusted medical diagnostic imaging scan sequence to acquire image data and reconstruct a medical diagnostic image of a patient utilizing the optimized medical diagnostics imaging scan sequence;
wherein adjusting the duration of one or more of the subsequences alters one or more of spatial resolution temporal resolution, contrast, a signal to noise ratio, and artifact sensitivity of at least one of the image data acquired by the scanner and the medical diagnostic image reconstructed from acquired image data.

2. The method according to claim 1, further including:
with the one or more computers, controlling a magnetic resonance diagnostic imaging scanner to acquire the image data for generating the medical diagnostic image of the patient.

3. The method according to claim 1, further including:
with a graphic user interface, prompting the user for acceptance of the adjusted scan sequence.

4. The method according to claim 1, further including:
executing the adjusted scan sequence with the diagnostic imaging scanner within the available time span.

5. A system for workflow management of a medical diagnostic imaging scanner, said system comprising:
one or more computers programmed to:
access a template comprising a medical diagnostic imaging sequence of handlings including alterable and non-alterable subsequences of a control sequence which controls a medical diagnostic imaging scanner to perform a medical diagnostic imaging sequence on a patient, each template having a corresponding duration;
access an available time span for executing said medical diagnostic imaging sequence;
calculate a difference between said available time span and a sum of corresponding handling durations;
assign an allowable duration for said medical diagnostic imaging sequence based on said difference;
optimize a duration of the subsequences of handlings such that the medical diagnostic imaging sequence temporally fits into the allowable duration including automatically adjusting advocation of at least one of the alterable subsequences;
control medical diagnostic imaging scanner with the optimized medical diagnostic imaging sequence to generate image data;
reconstruct the image data into medical diagnostic image, wherein adjusting the duration of one or more of the alterable subsequences alters one or more of spatial resolution, temporal resolution, contrast. a signal to noise ratio, and artifact sensitivity of at least one of the image data acquired by the scanner and the medical diagnostic image reconstructed from the acquired image data.

6. The system according to claim 5, further including:
at least one of a graphic user interface which interacts with the one or more computers to flag one or more of the handlings as being unalterable.

7. The system according to claim 5 further including:
a medical diagnostic scanner controlled by the one or more computers to image a patient using the medical diagnostic imaging scanner control sequence with at least one adjusted handling duration.

8. The according to claim 5 further including:
a display on which the subsequences and the corresponding durations of the optimized medical diagnostic imaging scan sequence are displayed and on which a prompt is displayed;
a user input device by which a user responds to the prompt to accept the adjusted scan sequence.

9. A non-transitory computer readable medium carrying software which controls one or more computers to:
access a template including a medical diagnostic imaging scan sequence which controls a medical diagnostic imaging scanner to perform a medical diagnostic imaging scan on a patient. the templated scan sequence including alterable and unalterable subsequences with their corresponding durations;
access an available time span for executing said medical diagnostic imaging scan sequence template;
calculate a difference between said available time span and a sum of the scan subsequence durations in said medical imaging scan template;
determine an allowable duration for said medical diagnostic imaging scan sequence based on said difference;
optimizing the medical diagnostic imaging scan sequence of said template to fit into the allowable duration by:
identifying the unalterable sub-sequences within said medical diagnostic imaging scan sequence;
subtracting the unalterable sub-sequence durations from the allowable duration yielding a remaining duration;
automatically adjusting the duration of at least one of the alterable sub-sequence within said medical diagnostic imaging scan sequence template yielding one or more adjusted alterable sub-sequences which temporally fits into said remaining duration;

combining unalterable sub-sequences with the adjusted alterable sub-sequences yielding an adjusted medical diagnostic imaging scan sequence:

controlling a medical diagnostic imaging scanner with the adjusted medical diagnostic imaging scan sequence to acquire image data and reconstruct a medical diagnostic image of a patient utilizing the optimized medical diagnostics imaging scan sequence:

wherein adjusting the duration of one or more of the sub-sequences alters one or more of spatial resolution temporal resolution, contrast, a signal to noise ratio, and artifact sensitivity of at least one of the image data acquired by the scanner and the medical diagnostic image reconstructed from acquired image data.

10. A system for medical diagnostic imaging workflow management for controlling medical diagnostic imaging, the system comprising:

one or more computers programmed to:

receive a template including an original medical imaging scan sequence which controls a medical diagnostic scanner to perform an imaging procedure on a subject, the original medical imaging scan sequence template including a plurality of subsequences, at least one of the subsequences being denoted as being an unalterable subsequence and at least one of the subsequences being an alterable subsequence, receive an available time span in which to perform the original medical imaging scan sequence, compare the available time span with an original sequence duration of the medical imaging original scan sequence template, in response to the original medical imaging sequence template duration being longer than the available time span, shortening at least one of the alterable subsequence to generate an optimize scan sequence that controls the medical imaging scanner to acquire medical image data in the available time span for reconstruction into a medical image of the subject, wherein adjusting the duration of one or more of the alterable subsequences alters one or more of spatial resolution, temporal resolution, contrast, a signal to noise ratio. and artifact sensitivity of at least one of the image data acquired by the scanner and the medical diagnostic image reconstructed from the acquired image data, wherein adjusting the duration of one or more of the alterable subsequences alters one or more of spatial resolution, temporal resolution, contrast, a signal to noise ratio, and artifact sensitivity of at least one of the image data acquired by the scanner and the medical diagnostic image reconstructed from the acquired image data.

11. The system according to claim 10, further including:

a display controlled by the one or more computers to display an indication of at least one of the subsequences and a duration of the at least one subsequence.

12. The system according to claim 10, further including:

a display controlled by the one or more computers to display a prompt which prompts a user to accept the optimized medical imaging scan sequence.

13. The system according to claim 12, further including:

a user input device by which a user inputs to the one or more computers an acceptance of the optimized medical imaging scan sequence.

14. The system according to claim 10, further including:

a medical diagnostic imaging device controlled by the one or more computers to perform the optimized medical imaging scan sequence to generate at least one of the medical image data and the medical image of the subject in the medical diagnostic imaging device.

* * * * *